United States Patent
Hickok et al.

(10) Patent No.: US 6,227,855 B1
(45) Date of Patent: May 8, 2001

(54) INSTRUMENT REMOVAL SYSTEM

(76) Inventors: Teresa R. Hickok, 4106 Paseo De La Vista, Bonita, CA (US) 91902; Clifford J. Ruddle, 227 Las Alturas Rd., Santa Barbara, CA (US) 93103

( * ) Notice: Subject to any disclaimer, the term of this patent is extended or adjusted under 35 U.S.C. 154(b) by 0 days.

(21) Appl. No.: 09/574,956

(22) Filed: May 19, 2000

(51) Int. Cl.[7] ................................. A61C 3/00; A61C 5/02
(52) U.S. Cl. ............................................. 433/141; 433/224
(58) Field of Search ..................................... 433/102, 141, 433/224

(56) References Cited

U.S. PATENT DOCUMENTS

| | | | |
|---|---|---|---|
| 4,746,292 | * | 5/1988 | Johnson ................................. 433/224 |
| 5,382,161 | * | 1/1995 | Roane ................................. 433/224 X |
| 5,879,160 | | 3/1999 | Ruddle ................................. 433/141 |

* cited by examiner

Primary Examiner—Nicholas D. Lucchesi
(74) Attorney, Agent, or Firm—Freling E. Baker; Baker & Maxham

(57) ABSTRACT

An instrument removal tool includes a hollow tube defining a lumen having a bottom end, a top end, and a cutout spaced from the bottom end; the hollow tube having an outer diameter sized to be received in the root canal, an inner diameter sized to admit an instrument into the lumen, and a wall width at the bottom of the tube sized to allow the bottom end of the hollow tube to pass over the top of the instrument such that at least the top of the instrument is received in the lumen of the tube, and an elongated shaft sized to be received in the hollow tube from the top end of the tube; the shaft having a length sufficient to extend beyond the cutout in the hollow tube, the shaft having a bottom end and a top end; the bottom end of said shaft being tapered and having a rounded end to urge a top end of the instrument into the cutout; the shaft and tube cooperating to grasp the instrument.

22 Claims, 3 Drawing Sheets

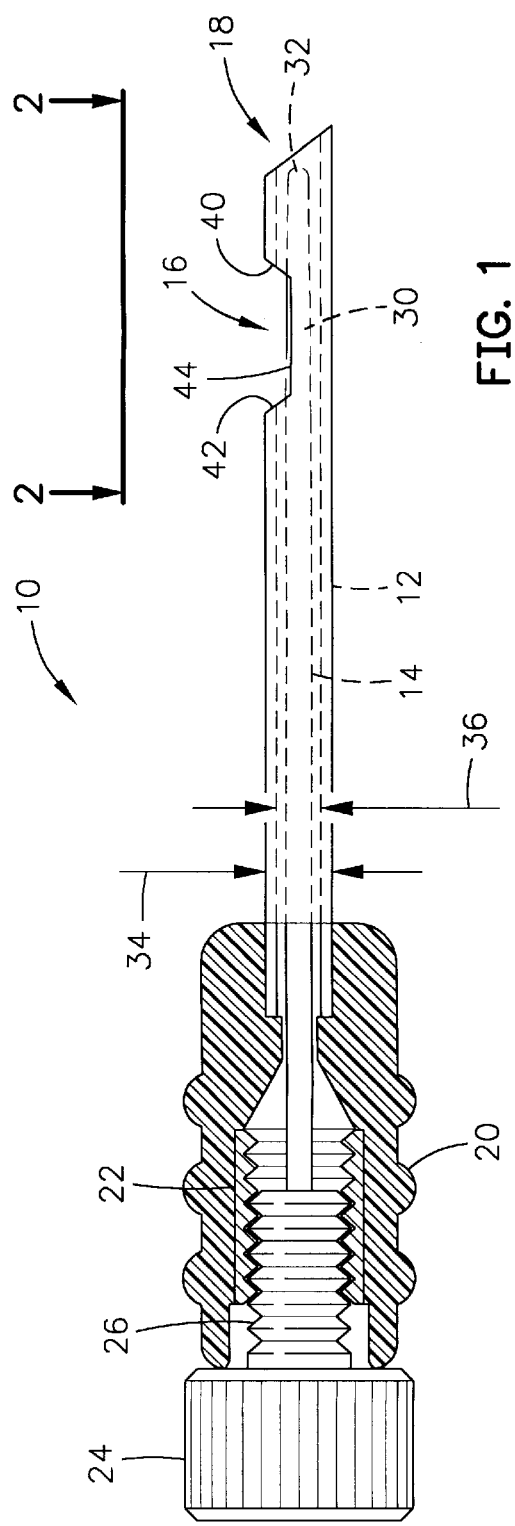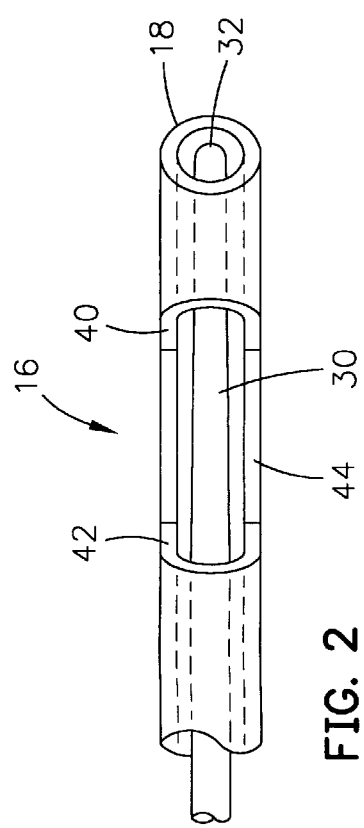

INSTRUMENT REMOVAL SYSTEM

BACKGROUND OF THE INVENTION

1. Field of the Invention

The present invention generally relates to dental tools and instruments and pertains particularly to a method and apparatus for removing obstructions, such as portions of instruments that break off and become stuck during endodontic and retreatment procedures, from root canals. More particularly, the invention relates to a set of microendodontic instruments precisely designed and machined to remove a broken instrument from deep within the root canal space.

2. Discussion of the Related Art

The human tooth is subject damage and injury from many sources over its life. A tooth comprises a crown and root, with the crown having a thin outer layer of enamel covering an underlying tubular dentine. The root's outer layer is comprised of a thin layer of cementum which covers the radicular dentine. Located generally central within these hard tissue structures is a soft tissue called the dental pulp which provides the vascular support and neural supply for the tooth.

The dental pulp is the most vulnerable and may be injured, requiring various treatments or repairs. Options for treatment include palliative emergency care, endodontics (i.e., root canal treatment), or extraction. Retreatment or extraction is necessary when prior treatment fails. Root canal treatment and retreatment includes cleaning and shaping of the root canal space with instruments commonly referred to as "files". There are a great variety of file choices ranging from different metals to flute configurations and geometries, tapers, lengths, and handle designs. During cleaning and shaping, the potential for file breakage is always present.

Retrieving broken instruments or other intercanal obstructions, such as gates glidden drills, lentulo spirals, silver points, and obturation carriers, pose formidable challenges because instruments can break at any point in the canal. If the coronal end of the broken instrument is near the crown of the tooth, the instrument can be removed fairly easily using traditional or conventional techniques. However, if the instrument breaks deep within the root canal, for example, where the canal begins to bend or curve, extraction of the instrument becomes much more difficult.

There has not been available any retrieval tools that can reach deep into the root canal, and thus are useless for broken instruments. Also, if the practitioner was still in the process of cleaning and shaping the root canal when the instrument broke, there can be bacteria, pulp, endotoxins, etc. deeper in the root canal that still needs to be removed. Thus, breakage of the instrument deep within the root canal can severely impact the outcome of the endodontic procedure. Typically, such instrument breakage results in tooth extraction or apical surgery to seal off the end of the root to prevent the bacteria, pulp, endotoxins, etc. from leaking out the end of the canal.

Some instrument retrieval techniques have been developed over the years. However, many of these methods were crude, ineffective, and limited by restricted space. Traditionally, small files were used in efforts to either bypass or eliminate broken instruments. In other efforts, varying diameter tubes have been proposed for placing over the most coronal end of the obstruction to be used in a variety of ways to retrieve obstructions. The tubes have been attached to the obstruction by various means such as glue, mechanical friction, or internal threads which engage certain broken instruments. For instance in U.S. Pat. No. 5,879,160 a system is proposed using a hollow tube in which a plunger with a beveled end is slid in order to engage the obstruction. However, the system requires the plunger to be slid into the tube and aligned so that the bevel is oriented towards the obstruction in order to force it into a cutout. This limitation makes the system more difficult to use because it requires radial alignment of the tube and plunger in accordance with each other as well as the obstruction. It is also less effective because failure results when the beveled edge fails to force the obstruction into the cutout. Moreover, it is less successful because there is no mechanism for securing the plunger to the tube when engaging the obstruction.

Frequently, such efforts, even when successful, weakened roots due to overzealous canal enlargement, which in turn predisposed the tooth to subsequent root fractures and, ultimately extraction of the tooth. Additionally, prior techniques lead to perforation of the root or the creation of ledges within the root canal, altering prognosis. Moreover, if retrieval efforts were unsuccessful, cleaning and shaping procedures and obturation are compromised putting the ultimate prognosis in doubt. Furthermore, a small but statistically significant number of broken instruments can not be retrieved even with all of these innovations, technologies, and techniques.

Therefore, a more successful, effective, and easy to use tool and method for removing broken instruments and other intercanal obstructions from root canal systems is needed.

SUMMARY OF THE INVENTION

The present invention solves the problem of difficult and failed retrieval of obstructions from root canals. Broadly, the present invention provides a superior tool and method for removal of broken dental instruments that are stuck in root canals.

In accordance with a primary aspect of the present invention, an instrument removal tool is provided comprising a hollow tube defining a lumen having a bottom end, a top end, and a cutout spaced from the bottom end; the hollow tube having an outer diameter sized to be received in the root canal, an interdiameter sized to admit an instrument into the lumen, and a wall width at the bottom of thereof sized to allow the bottom end of the hollow tube to pass over the top of the instrument such that at least the top of the instrument is received in the lumen of the tube; an elongated shaft sized to be received in the hollow tube from the top end of the tube; the shaft having a length sufficient to extend beyond the cutout in the hollow tube, the shaft having a bottom end and a top end; the bottom end of the shaft being tapered and having a rounded end to urge a top end of the instrument into the cutout; the shaft and tube cooperating to grasp the instrument.

The tool uses a thinner shaft with a tapered bottom section with a rounded end to "sneak up" on the broken instrument portion and pinch it into a cutout 16 or against the tube inner wall. The tool also provides for threads near the top of the shaft and tube so that the shaft may be screwed into the tube to help pinch the instrument portion towards the cutout to with increased force between the shaft and inner tube wall. The tool also employs an angular cutout to enhance securing of a broken instrument for removal.

BRIEF DESCRIPTION OF THE DRAWINGS

The nature, goals, and advantages of the invention will become more apparent to those skilled in the art after considering the following detailed description when read in connection with the accompanying drawing in which like reference numerals identify like elements throughout, wherein:

FIG. 1 is a side elevation view of an instrument removal tool showing an elongated shaft with a handle, threads, a tapered section, and a rounded end inserted and screwed down into a hollow tube with a handle, threads, and cutout;

FIG. 2 is a side elevation view of the hollow tube of FIG. 1, offset 90-degrees and taken along line 2—2 if FIG. 1 showing the cutout;

DETAILED DESCRIPTION OF THE PREFERRED EMBODIMENTS

General

Figure 3:
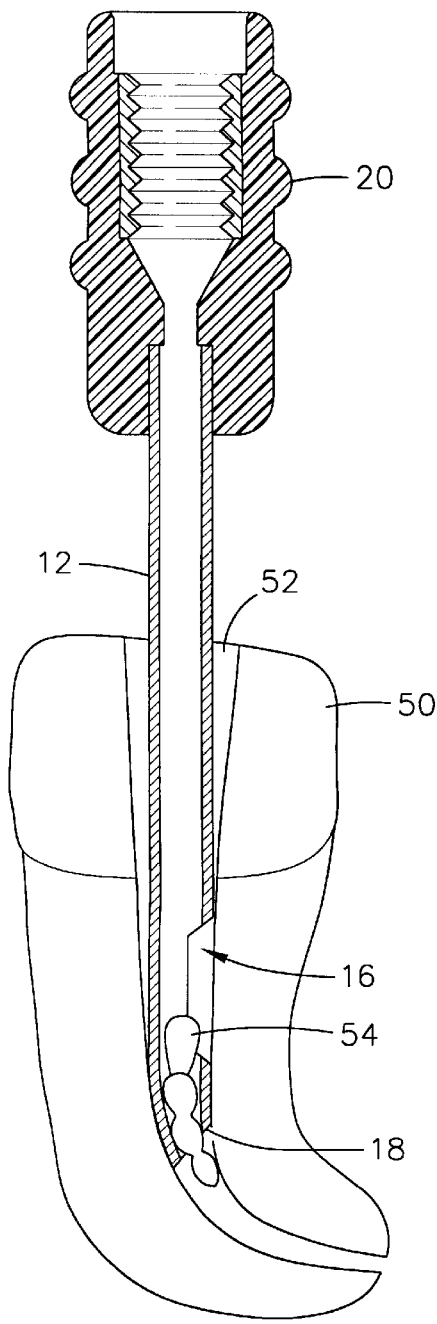
FIG. 3 is a cross-sectional view of the hollow tube placed in a human tooth root canal for removal of a root canal obstruction.

As shown in the drawing for purposes of illustration, an instrument removal tool and method according to the invention provides for the removal of obstructions from a tooth root canal. A tool according to the invention provides superior shaft design, superior cutout design, superior securing of the shaft to the tube, and increased gripping of the obstruction by the tool.

Referring to the drawings, and particularly FIG. 1, there is illustrated an instrument removal tool or system in accordance with one embodiment of the invention designated generally by the numeral 10. The tool comprises an elongated hollow tube 12 component and an elongated shaft 14 component for inserting into the tube. The hollow tube has a cutout 16 spaced a distance short from its open bottom end 18. At its top end the tube has a tube handle 20 to enable grasping and manipulation of the tube. Tube threads 22 may be formed or placed along the inside and a distance below the top end of the tube or tube handle. Similarly, the shaft has a shaft handle or knob 24 and may have shaft threads 26 a distance below the shaft handle for engaging the tube threads 22. The bottom of the shaft has a tapered section 30 and a rounded end or top 32.

The interior of the hollow tube 12 defines a lumen with an open bottom end 18, a top end, and a cutout 16 spaced a short distance from the bottom end. The cutout is preferably positioned between about one to two tube diameters from the end of the tube. The outer diameter 34 of the hollow tube is sized so that it can be inserted into a human tooth root canal. The inter-diameter 36 of the tube is sized so that an obstruction or portion of instrument can be introduced into the lumen for removal. Similarly, the tube wall width near the bottom is sized to allow the bottom end 18 of the hollow tube to pass over the top portion of an obstruction so that at least the top of the obstruction can be received within the lumen and preferably extend at least to the cutout. Furthermore, the tube bottom end 18 may vary in shape. For instance, the bottom end may be beveled, as illustrated in FIG. 1, in order to help position an obstruction towards the cutout 16. Alternatively, the end may be grooved to define cutting edges for removing tissue around an obstruction to assure that the tube end 18 can be pushed down and receive the top of the obstruction into the tube lumen.

The tube 12 is also preferably provided with a handle 20 at its top end to provide for easier manipulation and more force when maneuvering the tube to access the top portion of an obstruction. In embodiments having threads on the tube and shaft, a tube handle 20 also allows more torque to be applied when screwing the shaft 14 into the tube. The increased torque translates to more movement and/or pinching force applied to an obstruction when forcing the obstruction into the cutout or gripping it between the shaft and the tube wall. Moreover, the interdiameter of the handle 20 can be greater than the diameter of the tube to provide other benefits. For instance, a handle 20 with an inter-diameter larger than that of the tube 12 can be threaded 22 to provided more thread surface for engaging the shaft threads 26, leading to increased tool reliability, accuracy, and screwing torque and power.

Furthermore, it is preferred that the hollow tube 12 be slightly flexible, to slightly bend as shown in FIG. 3, to accommodate the curves in the root canal 52 when the tube is extended into the tooth to access the top end of an obstruction 54. The tube handle 20 can also be designed with protrusions, scoring, or other devices so that the handle and tube can be more forcefully manipulated.

Figure 4:
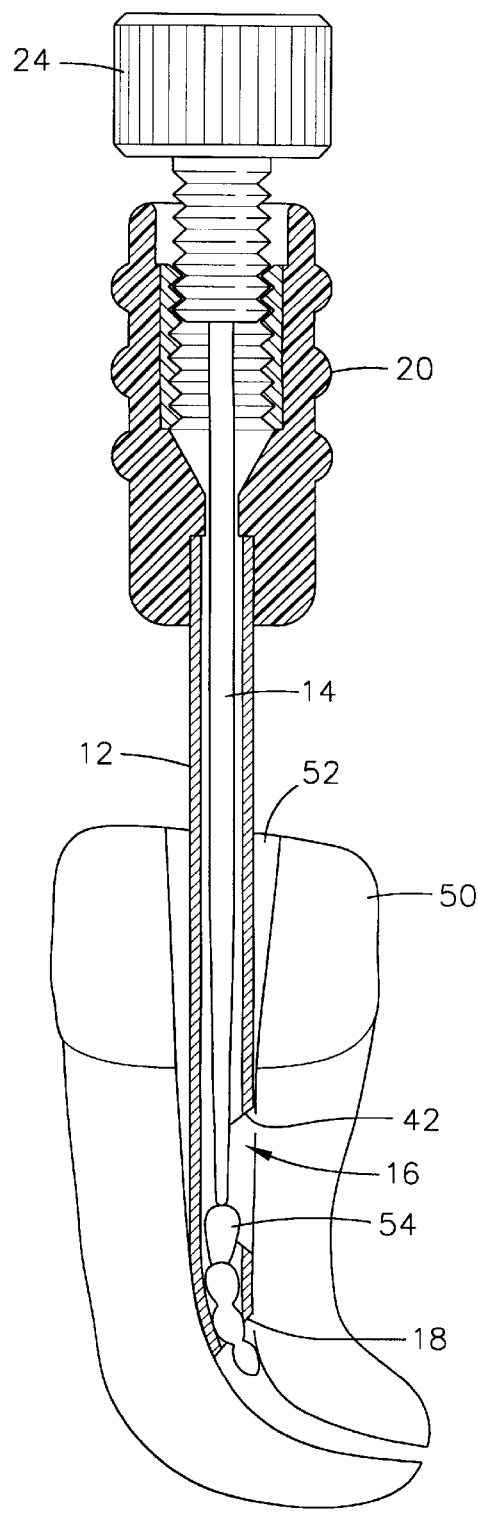
FIG. 4 is a cross-sectional view of the hollow tube and shaft in a human tooth root canal, showing the application of the rounded end of the shaft to the obstruction within the tube.
Figure 5:
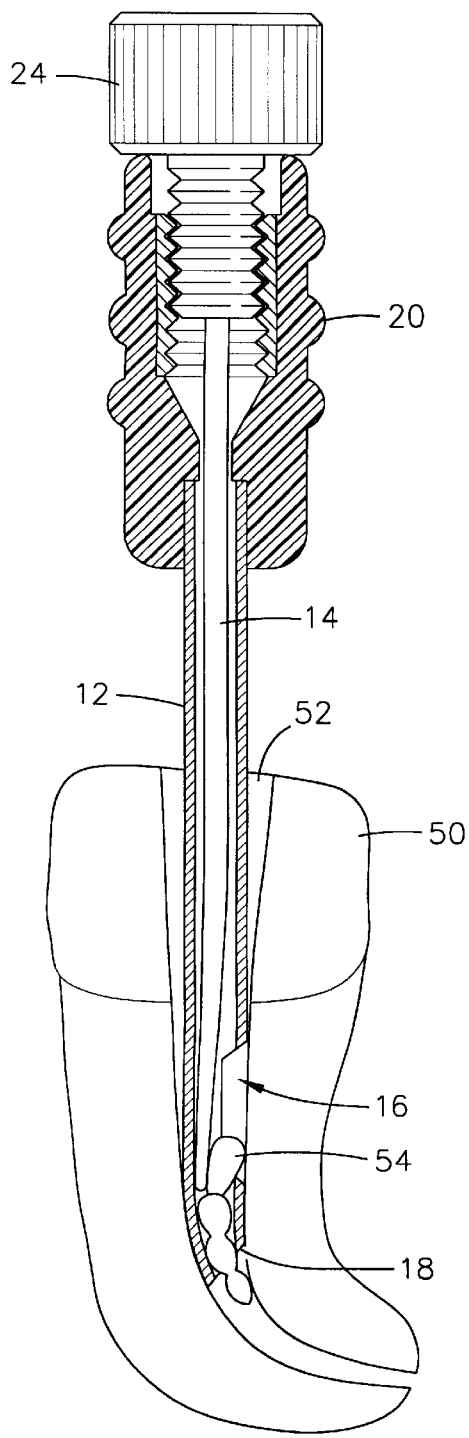
FIG. 5 is a cross-sectional view of the hollow tube and shaft in a human tooth root canal, showing the shaft screwed down into the tube in order to grasp the obstruction in the cutout for removal.

As shown in FIG. 1, the elongated shaft 14 is sized to be received in the hollow tube 12 from the tube's top end. Like the tube, the elongated shaft is also preferably slightly flexible so that it can flex in order to better grasp an obstruction and can accommodate the curves in the root canal when extended into the flexible tube to grip broken instruments. The shaft may have a variety of lengths ranging from long enough to extend just to the top edge of the cutout 42, to long enough to extend beyond the bottom end of the hollow tube 18. Similarly, the shaft diameter can vary from just small enough to fit into the tube, to ⅔ of the tube inter-diameter 36, or even less than half the tube inter-diameter 36 in order to allow the shaft to flex and move the instrument portion within the gap between the shaft and tube inner wall. Referring to FIGS. 4 and 5, one of the benefits of this improved shaft is that its tapered section 30 and rounded end 32 help urge the top end of a broken instrument 54 into the cutout 16, thus allowing the shaft and tube to better cooperate at grasping the instrument.

Additionally, the shaft is preferably threaded at 26 for engaging a set of tube threads 22. The shaft threads 26 can have a diameter larger than that of the shaft in order to engage larger diameter tube threads (placed either in the wider tube or tube handle) to provide more thread surface for more reliability, accuracy, and shaft screw torque and power. Moreover, these threads can be positioned at various distances from the shaft rounded end 32. For instance, they can be placed so that the shaft rounded end 32 is above the top edge 42 of the cutout when the threads engage, or alternatively, so that the rounded end 32 passes by the cutout 16 before the threads engage.

The shaft is also preferably constructed with a large enough knob 24 at the top end above the shaft threads 26 in order to allow more torque to be used when screwing the shaft into the tube. This allows more movement and pinching power to be transferred to the obstruction when forcing the obstruction into the cutout or gripping it between the shaft and the tube wall, as shown in FIG. 5. Also, the shaft handle or grip can be designed with protrusions, scoring, or other means to increase shaft handle 24 gripping force.

Referring to FIGS. 1 and 2 of the drawings, an embodiment of the cutout 16 is shown with a planar surface 44 parallel to the tube axis, and a bottom edge 40 and a top edge 42 corresponding to the bottom end 18 and top end of the tube. Optimally, the bottom edge 40 and top edge 42 angle outward away from the planar surface 44 or the axis of the tube at an angle of about 45-degrees. In other words, the cutout has a flattened planar surface 44 and edges so that when viewed from a side elevation it has a profile shaped about as follows: \/. The advantages of this improved cutout design are superior instrument grasping capability and easier manufacturing. For example, the angular cutout 16 enhances the tool's ability to secure the top end of a broken instrument for removal by giving the cutout 16 edges for grasping the instrument.

In addition, differently sized tube and shaft combinations can be used in order to fit into differently sized root canals and remove variably sized obstructions. For instance, the tube outer diameter 34 can range between about 0.032 and 0.042 inch, depending on root canal size. Correspondingly, the tube inter-diameter 36 can range between about 0.025 and 0.037 inch, depending on the radius of the top end of the obstruction 54 to be removed. Similarly, the preferred tube length is around 0.945 inch. It is also preferred that the tube bottom end 18 be beveled at an angle depending on the tube outer diameter 34 and length, but preferably at an angle of approximately 40 degrees.

The tube handle 20 outer diameter is preferred at roughly 0.170 inches. Correspondingly, the tube handle inter-diameter is preferably around 0.090 inches. Also, correspondingly, the preferred tube thread 22 depth is a minimum of about 0.200 inches. Similarly, the preferred tube handle 20 length is approximately 0.375 inches and the preferred length of the tube thread 22 section is about 0.150 inches.

Likewise, there is a preferred shaft length of about 1.060 inches. The elongated shaft 14 outer diameter can range between roughly 0.0150 and 0.0200 inches, depending on the interdiameter of the tube and the radius of the top end of the obstruction to be removed. Correspondingly, the preferred shaft tapered section 30 length is about 0.175 inches and the shaft rounded end 32 is preferably rounded at an angle of approximately 90 degrees. Also, the shaft tapered section 30 tapers down to a rounded end 32 diameter ranging between around 0.009 and 0.014 inches, depending on the diameter of the shaft, the inter-diameter of the tube, and the radius of the top end of the obstruction to be removed.

For the shaft handle or knob 24, the outer diameter is preferred at about 0.250 inches. Similarly, the preferred shaft knob 24 length is around 0.155 inches. Additionally, the shaft thread 26 radius is preferably about 0.090 inches. Correspondingly, the length of the shaft thread 26 section is preferably about 0.180 inches and the shaft thread 26 depth is preferably a minimum of about 0.200 inches deep.

In addition, the cutout bottom edge 40 preferably begins a distance of about 0.025 inches from the tube bottom end 18. Correspondingly, it is preferred that the cutout top edge 42 ends a distance from the tube bottom end 18 of around 0.105 inches and that the cutout extends on the tube surface for roughly 0.080 inches from the ends of its top to bottom edges. Also, the cutout planar surface 44 preferably ranges about 0.050 inches in length. Accordingly, the bottom edge 40 and top edge 42 angle outward away from the planar surface 44 or axis of the tube, preferably at an approximately 45 degree angle. Also, the planar surface 44 can be cutout at a range in distance below the tube outer surface between 0.017 and 0.014 inches.

The instrument removal tool is simple and easily fabricated and may be packaged in kits having different diameter tubes and shafts as necessary. A kit may also contain a separate trephine for clearing space around to top end of a broken instrument or obstruction 54 within the root canal 52 as shown in FIG. 3, for superior tube open end 18 access. Manufacture of the tube handle 20, tube threads 22, shaft threads 26, and/or shaft handle 24 can be done separately and then assembled later. Furthermore, these components can be manufactured from nickel titanium or stainless steel. The handles can alternatively be made of a plastic.

Referring to FIG. 3, a method of removing an instrument from a tooth 50 root canal using the tool 10 involves a set of steps. First, assure that there is enough of a gap in the root canal 52 between the canal edge and coronal end of the broken instrument 54 or obstruction so that the hollow tube's bottom end 18 can be pushed down entering the obstruction coronal top end into the tube lumen. Tissue between the obstruction 54 and root canal 52 can be removed, if necessary, using a separate trephine or a hollow tube 12 having grooves that define cutting edges at its bottom end 18.

Second, the hollow tube is inserted 12 into the root canal 52 so that the bottom end 18 admits the obstruction 54 or instrument into the lumen. Although it is possible to grip the obstruction 54 if only a portion of it is admitted into the lumen, it is preferred that enough of the obstruction be received into the tube to extend at least to the cutout 16, as illustrated in FIG. 3. A beveled tube bottom end 18 may help position the obstruction into the lumen and towards the cutout 16 especially in a curved canal. Furthermore, extending a flexible hollow tube 12 into the root canal 52 will accommodate the curves in the canal to obtain better access the top end of the obstruction 54.

Third, as shown in FIG. 4, the rounded end of the shaft 14 is inserted through the top end of the hollow tube 12 so that the shaft and hollow tube cooperate to mechanically grasp or engage the obstruction 54. The elongated shaft 14 is provided with threads 26 near its top end for engaging a set of tube threads 22 running along the inside of the tube 12 or tube handle 20. The advantage of this construction is that once the tube is properly placed in the root canal, the threads will allow the shaft to be screwed down into the tube gripping the obstruction. The threads can be placed near the top of the shaft 26 and tube 22 to engage each other either before or after the shaft rounded end 32 passes by part of the obstruction 54. It is preferred for the threads to engage before the end 32 reaches an obstruction 54, as shown in FIG. 4, so that the rounded end 32 is rotating as it is screwed down past the upper portion of the obstruction 54. Either way, the objective is for the shaft rounded end 32 and tapered section 30 to urge and grip the top end of the obstruction 54 into the cutout 16 as shown in FIG. 5.

For example, in the embodiment illustrated in FIG. 5, the improved shaft 14 is flexible and has a diameter about half of the tube inter-diameter 36, a tapered bottom section 30, and a rounded end 32, so that while it is being screwed into the tube it will deflect to one side of the broken instrument portion and pinch it into the cutout, or against the tube inner wall. The motion and dynamics between the tube, shaft, and instrument during the rotational screwing of the shaft help pinch the instrument portion towards the cutout because there is space between the shaft and the tube wall for the flexible shaft and obstruction to share. Hence, as the shaft is screwed into the tube, the shaft and obstruction become slightly displaced away from each other. Then, the twisting shaft rotates itself and the upper end of the obstruction around the inside of the tube until the obstruction "pops" out of the cutout.

Figure 6:
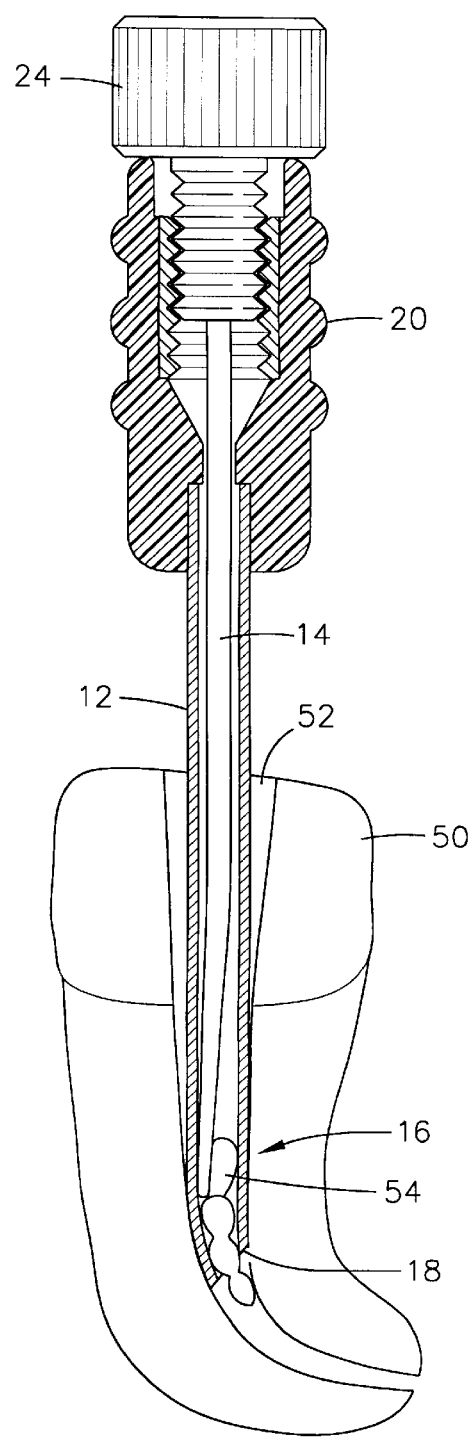
FIG. 6 is a cross-sectional view of the hollow tube and shaft in a human tooth root canal, showing the shaft screwed down into the tube in order to pinch the obstruction between the shaft and tube inner wall for removal.

Alternatively, if the obstruction does not "pop" out of the cutout, it is possible for the shaft to sufficiently pinch and grip the obstruction against the tube wall or cutout for removal. Referring to FIG. 6, this "pinching" is done by screwing the shaft 14 into the tube 12 until the tapered section 30 alongside the obstruction 54 gets thick enough to force the obstruction against the tube 12 inner wall. The goal is to grip the obstruction between the shaft and tube inner wall with such force that it is possible to remove the obstruction 54 by pulling the hollow tube 12 and screwed in shaft 14 from the root canal 52 with the obstruction grasped between them. So, once the broken instrument or obstruction is pressed into the cutout 16, or sufficiently pinched between the shaft and tube wall, the obstruction 54 is removed when the tube and shaft are pulled up out of the tooth 50 root canal 52.

Optional embodiments may use mechanisms and methods other than threads for moving the shaft's rounded end 30 and/or tapered section 32 adjacent to the obstruction 54. Similarly, other it is mechanisms and methods to secure the shaft to the tube such as clasps, latches, or ribs and slots can be employed. It is also possible to forgo any securing mechanism or method, thereby allowing the practitioner to use "feel" to assure proper tube-shaft grasping or pinching of the obstruction and removal.

Therefore, as opposed to the previous designed bevel edged plunger requiring specific plunger to tube radial orientation, the improved tool's thinner shaft, tapered bottom, and rounded end, make it easier to use and more effective. Also, the addition of threads near the top of the shaft and tube allow the improved tool to rotate the instrument towards the cutout and to pinch the instrument against the inner tube wall making it more successful. Finally, the tool's superior tube cutout shape enhances its ability to secure a broken instrument for removal.

Other Embodiments

While preferred embodiments have been described above, it is to be understood that a latitude of modification and substitution is intended in the foregoing disclosure, and that these modifications and substitutions are within the literal scope—or are equivalent to—the claims that follow.

Accordingly, it is appropriate that the following claims be construed broadly and in a manner consistent with the spirit and scope of the invention herein described.

What is claimed is:

1. An instrument removal tool comprising:
   a hollow tube defining a lumen having a bottom end, a top end, and a cutout spaced from the bottom end; said hollow tube having an outer diameter sized to be received in the root canal, an interdiameter sized to admit an instrument into the lumen, and a wall width at the bottom of thereof sized to allow the bottom end of the hollow tube to pass over the top of the instrument such that at least the top of the instrument is received in the lumen of the tube; and
   an elongated shaft sized to be received in the hollow tube from the top end of the tube; the shaft having a length sufficient to extend beyond the cutout in the hollow tube, the shaft having a bottom end and a top end; the bottom end of said shaft being tapered and having a rounded end to urge a top end of the instrument into the cutout; the shaft and tube cooperating to grasp the instrument.

2. An instrument removal tool according to claim 1 wherein said tube has a beveled bottom end.

3. An instrument removal tool according to claim 2 wherein said shaft has a diameter that is less than ⅔ the diameter of the tube.

4. An instrument removal tool according to claim 2 wherein said shaft has length so that it may extend beyond the bottom end of said tube.

5. An instrument removal tool according to claim 2 wherein said elongated shaft has a length to position bottom end of said shaft below the bottom end of said cutout before engagement of said threads.

6. An instrument removal tool according to claim 2 further comprising a knob at the top end of said shaft and wherein said shaft threads are below said handle.

7. An instrument removal tool according to claim 2 wherein said tube, shaft, cutout, and threading are constructed so that said instrument will be caught between said shaft and said tube inner wall with enough force when said shaft is screwed into said tube to allow extraction of said instrument.

8. An instrument removal tool according to claim 2 further comprising a handle grip at the top end of said tube, wherein said tube threads are inside of said grip.

9. An instrument removal tool according to claim 2 wherein said cutout forms a planar surface parallel to the tube axis, and a bottom edge and top edge corresponding to the bottom and top ends of the tube; and wherein the cutout bottom and top edge angle outward away from the planar surface of the cutout at an angle of 45-degrees.

10. An instrument removal tool according to claim 1 wherein said elongated shaft further comprises threads a distance from its top end; and wherein said tube further comprises threads around its inner diameter a distance from its top end such that said shaft may be screwed down into said tube.

11. An instrument removal tool comprising:
   a hollow tube defining a lumen having a bottom end, a top end, and a cutout spaced from the bottom end; said hollow tube having an outer diameter sized to be received in the root canal and an interdiameter sized to admit an instrument into the lumen;
   an elongated shaft sized to be received in the hollow tube from the top end of the tube; the shaft having a length sufficient to extend at least to the top of the cutout in the hollow tube; and
   wherein said elongated shaft further comprises threads a distance from its top end; and wherein said tube further comprises threads around its inner diameter a distance from its top end such that said shaft may be screwed down into said tube.

12. An instrument removal tool according to claim 11 wherein said tube has a beveled bottom end.

13. An instrument removal tool according to claim 11 wherein said shaft has a diameter that is less than ⅔ the diameter of the tube.

14. An instrument removal tool according to claim 11 wherein said shaft has length so that it may extend beyond the bottom end of said tube.

15. An instrument removal tool according to claim 11 wherein said elongated shaft has a length to position bottom end of said shaft below the bottom end of said cutout before engagement of said threads.

16. An instrument removal tool according to claim 11 comprising a knob at the top end of said shaft and wherein said shaft threads are below said handle.

17. An instrument removal tool according to claim 11 wherein said tube, shaft, cutout, and threading are constructed so that said instrument will be caught between said shaft and said tube inner wall with enough force when said shaft is screwed into said tube to allow extraction of said instrument.

18. An instrument removal tool according to claim 11 further comprising a grip at the top end of said tube, wherein said tube threads are inside of said grip.

19. An instrument removal tool according to claim 11 wherein said cutout forms a planar surface parallel to the tube axis, and a bottom edge and top edge corresponding to the bottom and top ends of the tube; and wherein the cutout bottom and top edge angle outward away from the planar surface of the cutout at an angle of 45-degrees.

20. A method of removing an instrument from a root canal comprising the steps of:

widening the root canal around a coronal end of the instrument;

selecting inserting a hollow tube into the root canal, the tube having a bottom and a top end, and a cutout spaced from the bottom end; said tube having an inner diameter at said bottom end sized to admit said instrument to be received within said bottom end of said tube; said tube being inserted into said root canal until at least a portion of said instrument is received within said tube and extents to said cutout;

selecting and inserting a shaft through said hollow tube to engage said instrument; said shaft having a bottom end and a top end; said shaft being passed through the top end of said tube until the bottom end of said shaft passes by a portion of said instrument; the bottom end of said shaft being tapered and having a rounded end to urge a top end of the instrument into the cutout; said shaft and hollow tube cooperating to mechanically grasp said instrument;

removing the hollow tube and shaft from the root canal with the instrument grasped thereby.

21. A method of removing an instrument from a root canal according to claim 20, wherein:

the steps of selecting the hollow tube includes selecting the tube having threads a spaced from the top end for engaging threads of a inserted shaft; and the steps of selecting the shaft includes selecting the shaft having threads at the top end for engaging said threads of said tube.

22. A method of removing an instrument from a root canal according to claim 20, comprising the steps of:

twisting said shaft relative to said tube thereby screwing said shaft down into said tube until said instrument is mechanically grasped by said shaft and hollow tube; and removing the hollow tube and shaft from the root canal with the instrument grasped thereby.

* * * * *